United States Patent [19]
Elmaleh et al.

[11] Patent Number: 4,515,697
[45] Date of Patent: May 7, 1985

[54] METHOD FOR FLOCCULATING MICROSCOPIC PARTICLES IN SUSPENSION IN A LIQUID AND APPLICATION TO THE COLLECTION OF PHYTOPLANKTON MICROALGAE AND ZOOPLANKTON AND FOR THE PURIFICATION OF USED WATER

[75] Inventors: Samuel Elmaleh, Clapiers; Alain D. Grasmick, Montferrier, both of France

[73] Assignee: David Gozal, Madrid, Spain

[21] Appl. No.: 461,628

[22] Filed: Jan. 27, 1983

[51] Int. Cl.$^3$ .............................................. B01D 23/10
[52] U.S. Cl. ................................. 210/768; 210/792; 210/805
[58] Field of Search .................. 210/792, 805, 768

[56] References Cited

U.S. PATENT DOCUMENTS

| | | | |
|---|---|---|---|
| 1,563,849 | 1/1925 | Hartman | 210/805 |
| 3,737,039 | 6/1973 | Hirs | 210/792 |
| 4,372,859 | 2/1983 | Sugimoto et al. | 210/805 |

FOREIGN PATENT DOCUMENTS

| | | | |
|---|---|---|---|
| 11566 | 1/1979 | Japan | 210/792 |
| 0349781 | 6/1931 | United Kingdom | 210/792 |

*Primary Examiner*—Ivars Cintins
*Attorney, Agent, or Firm*—Lackenbach Siegel Marzullo Presta & Aronson

[57] ABSTRACT

Method for flocculating microscopic particles in suspension in a liquid and application to the collection of phytoplankton microalgae and of zooplankton and for the purification of used water.

One passes a first liquid comprising microscopic particles in suspension through a fixed granular layer (2) up to partial or complete clogging of said granular material by said microscopic particles; one unclogs at least partially said granular material in a fixed layer by passing a second liquid therethrough, moving in the same direction as the first liquid, but at a higher speed than the first; and one recovers below said layer flocculated aggregates of said microscopic particles and a liquid outflow (6).

14 Claims, 3 Drawing Figures

METHOD FOR FLOCCULATING MICROSCOPIC PARTICLES IN SUSPENSION IN A LIQUID AND APPLICATION TO THE COLLECTION OF PHYTOPLANKTON MICROALGAE AND ZOOPLANKTON AND FOR THE PURIFICATION OF USED WATER

SUMMARY OF THE INVENTION

The invention relates to a method for floculating microscopic particles in suspension in a liquid. The invention also concerns the application of this method to the collection of living particles which are suspended in sweet, brackish or salt water, especially microalgae which form the phytoplankton and microscopic animals which form the zooplankton.

The invention also relates to the method of purifying used water.

BACKGROUND OF THE INVENTION

Microalgae are of considerable economic interest because their cells contain molecules of great value, such as medicamental substances, hydrocarbons (glycerol in Dunaliella of salt marshes), proteins which can serve as food for animals or humans, and which can also serve as a substrate for an anaerobic fermentation producing methane, a combustible gas.

In basins for purification of used water, the highest concentrations of microalgae are found which are susceptible of being found in nature (200 to 600 mg/l of dry product with 2.10 algae cells per cubic centimeter). The process of purification is thus accompanied by a large primary production of microalgae estimated as lying between 50 to 150 tons/ha/year. This phytoplankton can be utilized for the production of zooplankton in aquaculture (mainly Rotifera, Copepoda and Daphnia). These animals groups constitute an adequate alimentary chain for feeding young shell fish and fish, but the production of this alimentary chain is under presently known methods costly, sophisticated and difficult to carry out.

As a matter of fact, the most delicate problem encountered in these methods which constitute a form of exploitation of solar energy, is the collecting of microalgae.

The economic difficulties will now be pointed out which come up in this collecting by making reference to the methanization of microphytes which, with respect to the production of renewable energy, have been considered with considerable interest during the past years.

In the most favorable cases—control of the collected species, gathering by methods which require very little power, no drying—the raw energetic content of the production of algae (total quantity of enthalpy used for maintaining the production system in operation, beginning with natural raw material), is about 18 MJ/kg. By methanogene fermentation, 60% of the lower caloric power—a heat gained by combustion with the water formed being in the state of vapor—can be recovered, this caloric power rising to 23.2 MJ/kg, which is 13.9 MJ/kg.

This means, for example, that a mass of 80 kg of microphytes allows the production of 1 GJ by methanization, but that its production having required 1.44 GJ, the total energy balance is negative, because essentially, of the complexity of the separation of microphytes from the aqueous medium.

Because of their dimensions (10–30 $\mu$m) and their typical characteristics (living organisms), the microscopic algae pose difficult problems of separation. Certain methods already tested have shown to yield either small results or they consume lots of energy (this is the case of centrifugal decanting or of flotation, tested on a large scale for the separation of plankton).

In the treatment of making water potable, microsifting has been used with success for several years with the primary objective of the elimination of algae. The eliminated suspension materials are recovered in a more concentrated state but in form of a liquid still with a relatively low charge (concentration 20 to 30).

With a filtration on granular material, better results are attained, but at the price of a greater consumption of energy. There again, a recuperation of retained material in suspension can be expected at a rate of concentration of 20 to 30.

The performance of certain of the cited methods can be improved by adding chemical reagents to allow floculation of the algae. But this operation increases the cost of production considerably and may render the use of the product in a food chain impossible.

As a result, if a concentrated suspension of several tens of grams per liter is of any interest, methods such as microsifting or filtering can apply. If a stronger concentration is to be attained, it must be said, that up to this day no method exists which meets both technical and economic requirements.

DISCLOSURE OF THE INVENTION

It is therefore an object of the present invention to obviate the preceding drawbacks and to provide a method for flocculating microalgae or other organic particles with similar properties without the addition or reagents, using little energy, and with such a modification of the physical properties of the microalgae that a simple decanting allows exceeding the rates of concentration in the order of 100, and this without changing their nutrient quality.

It is pointed out that flocculation is a complex phenomenon which leads to the formation of flakes, i.e. of a reticulated and porous structure. Under this description, one often confounds the phenomena of coagulation and of true flocculation whose effects are the creation of easily separable aggregates. For example, the physical-chemical treatment of used water comprises a flocculation phase which is obtained by adding to this water a suitable reagent (ferric chloride, aluminum sulfate, polyelectrolytes or others) and which is followed by a liquid-solid separation by decantation.

This clearing up by flocculation is particularly useful in the treatment of used water at a variable output, excluding the use of traditional biological methods. On the other hand, this type of treatment has considerable drawbacks in that cost is high, due to the consumption of flocculation agents.

The inventor has conceived a method of causing the flocculation of microscopic particles in suspension in a liquid which can be advantageously applied to the collection of living micro-organisms and wich does not require the addition of flocculation reagents.

Consequently, it is an object of the invention to provide a method for flocculating microscopic particles suspended in a liquid, characterized in that a first liquid containing microscopic particles in suspension is passed through a fixed granular layer up to partial or complete clogging of said granular material by said microscopic particles, in that said fixed granular layer is at least partially unclogged by passing a second liquid therethrough, moving in the same direction as the first liquid, but at a higher speed, and in that one recovers below said layer in the direction of passage of said liquids flocculated aggregates of said microscopic particles and an outflow of a liquid which is partially or totally free of said particles.

The second liquid may itself contain microscopic particles in suspension and may be identical to the first liquid having served to clog the granular materials. This applies in particular when the method according to the invention is carried out continuously, in which case a portion of the outflow which may contain any flocculate, can be recycled for being supplied to the granular material.

In the case of a continuous use of the method according to the invention, the granular material can remain as a fixed layer or expand by at most about 30% in volume, which means that the granular material is in a fluidized state.

The granular material can preferably be constituted of granular particles of about 0.005 and 3 cm and of a volume of about 1.1 g/cm³ or more. The exact dimensions and the nature of the particles as well as the speed of traversing the granular material, generally between 0.1 and 5 m/h (speed in a empty column) are chosen as a function of the treated suspension and the desired results. As a granular material, one can simply use natural sand. It is also possible to use other particles with sharp or rounded angles, for example ceramics or particles of calcinated or crushed clay.

Preferably, this method can be carried out in a vertical or inclined column which is either cylindrical or helical and which contains the granular material. This column is supplied at its base by the liquid to be treated, whereas the aggregates of flocculated particles are recovered at a higher level than that of the granular material, and the outflow of the purified liquid is evacuated at a still higher level. Although this form of carrying out the method according to the invention is the preferred one, a descending flux can also be applied.

In order to facilitate the concentration of the flocculate, the portion of the column where it is recovered in an ascending flux, has preferably a surface area which is larger than that of the portion which contains the granular material.

In its application for the collection of microalgae or zooplankton, the method according to the invention includes at least one additional phase of concentrating the flocculates separated from the granular material, for example by decantation, possibly—as has been indicated—right in the column in which the method is carried out. It is also possible to use other known concentration method which cannot normally be utilized for collecting microalgae or zooplankton in suspension because of the very low concentration of these suspensions.

In its application to the purification and the clearing of used water, the methods according to the invention does not require flocculation reagents and can therefore be operated at much lower cost than the usual methods which include a flocculation phase.

Figures 1, 2:
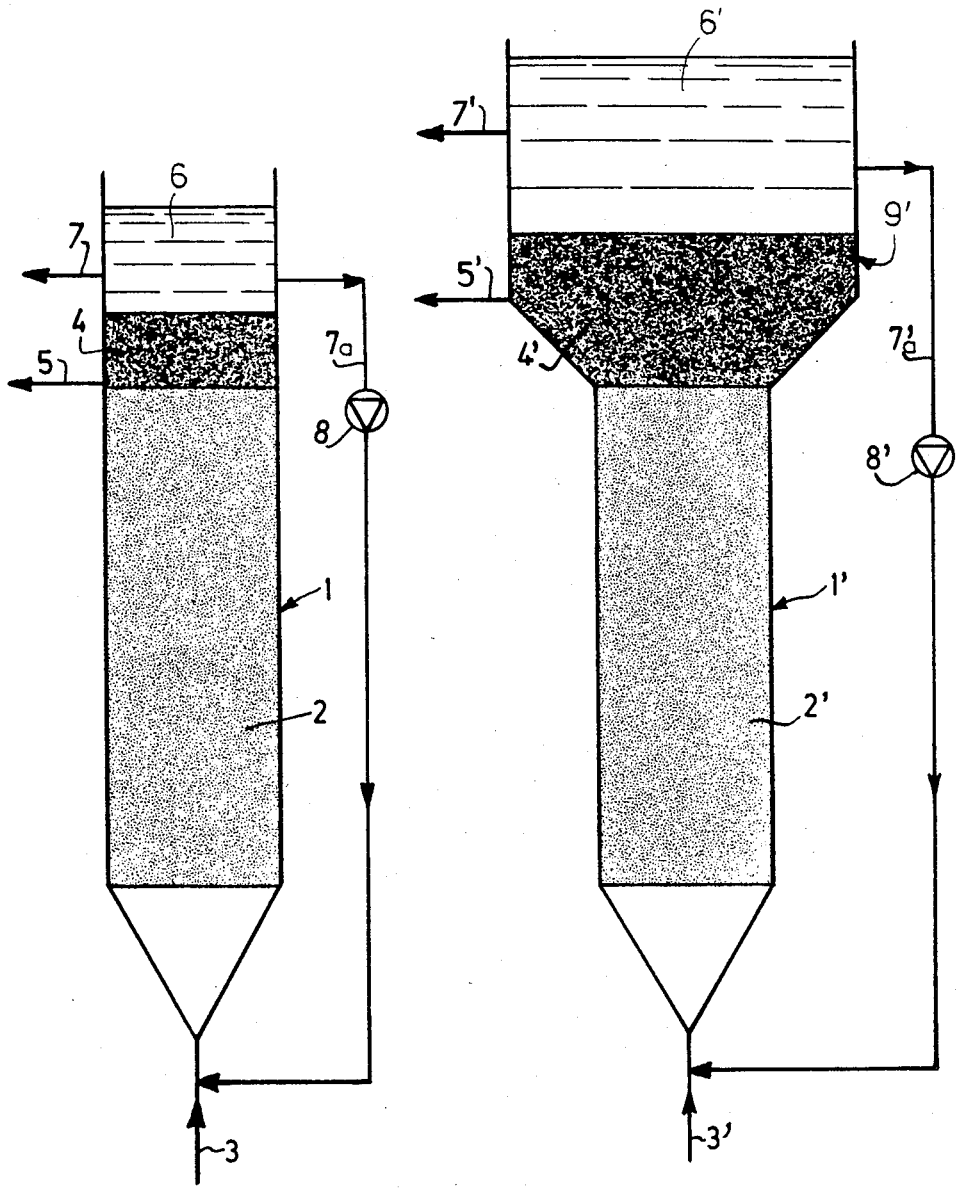
FIGS. 1 and 2 of the attached drawings are schematic views which illustrate two forms of carrying out the preferred method according to the invention.

The granular layer 2 is supplied with liquid through a pipe 3 connected to the base of the column.

In a first step, the granular bed 2 is supplied through a line 3 with a liquid containing microscopic particles in suspension which can be or cannot be identical with the liquid to be subsequently treated, and a filtration of the liquid traversing the fixed layer of solid particles is thus carried out. In this manner, a progressive clogging of the layer 2 is caused, and an increase in the loss of charging through the layer is noticed. The feeding is stopped when this loss of charging attains a predetermined value, corresponding to a partial clogging of the layer 2, or possibly after a complete clogging of said layer. In tests carried out by the inventor, the loss of charging corresponding to a satisfactory clogging of the layer 2 has been in the order of 50 cm of water height per meter of height of the granular layer.

After the granular layer 2 has been treated in this manner, it can be used to cause continous flocculation of a suspension of microscopic particles, such amicroalgae, which can differ or not differ from the suspension having served for clogging the layer 2.

The suspension to be treated is injected by conduit 3 at the base of the column 1 at a higher speed than that of the suspension which was used before to clog the granular layer at, normally, from 0.1 to 5 m/h.

It is surprising to observe the formation of a flocculate of microscopic particles from the suspension at the output of the granular layer. The flakes can have dimensions of between 1 and 5 mm, and by decantation they are separated at the top of the column 1 when they form a coating 4 which can be removed intermittently or continuously through a conduit 5. This flocculate coating 4 is surmonted by a coating 6 of liquid, at least partially purified, which is evacuated through the conduit 7. At least a portion of this liquid outflow can be recycled by a pump 8 and through a conduit 7a to the supply conduit 3 for recovering the floccuate which may be present there.

The granular layer 2 having served for the pretreatment of partial or total clogging can then be used continuously for flocculating the microscopic particles which are present in the supply suspension. The rate of concentration between the original suspension and the flocculate reaches, for example, several tens in the case of microalgae.

The reason for the phenomenon of flocculation is not completely clear, but it is assumed that the clogging of the granular layer and the partial unclogging which follows it have the effect of creating inside said layer paths which form as many preferential passages as the suspension to be treated uses. The only energy required is the one for ensuring the movement of the liquid through the layer, and it is therefore very low.

Under the conditions for carrying out the method, the layer 2 can remain fixed or undergo a slight expansion of about 30%; the coating can thus be fixed, prefluidified or fluidified.

The flocculate which is evacuated through the conduit 5 can be very easily concentrated by known methods of liquid-solid separation. A simple decantation allows to attain a rate of concentration of several hundreds for microalgae. The volume occupied by one gram of dry material, after 10 minutes of decantation in the test tube, is about 70 cm$^3$, which is a particularly interesting result.

FIG. 2 shows a preferred embodiment for carrying out the method according to the invention. In this figure the elements already described in connection with FIG. 1 having the same reference numerals following by a '.

The only substantial difference from FIG. 1 is that the column 1' which contains the granular layer 2' is enlarged above said layer and is surmounted by a column whose transverse section is greater than that of the column 1'. Under these conditions, the ascending speed of the liquid in the column 9' is smaller than that in the column 1', which has the effect of enhancing the concentration of the flocculate.

FIGS. 1 and 2 show one preferred form of carrying out the invention, in which the granular layer 2 or 2' is traversed by an ascending flux of liquid to be treated.

Figure 3:
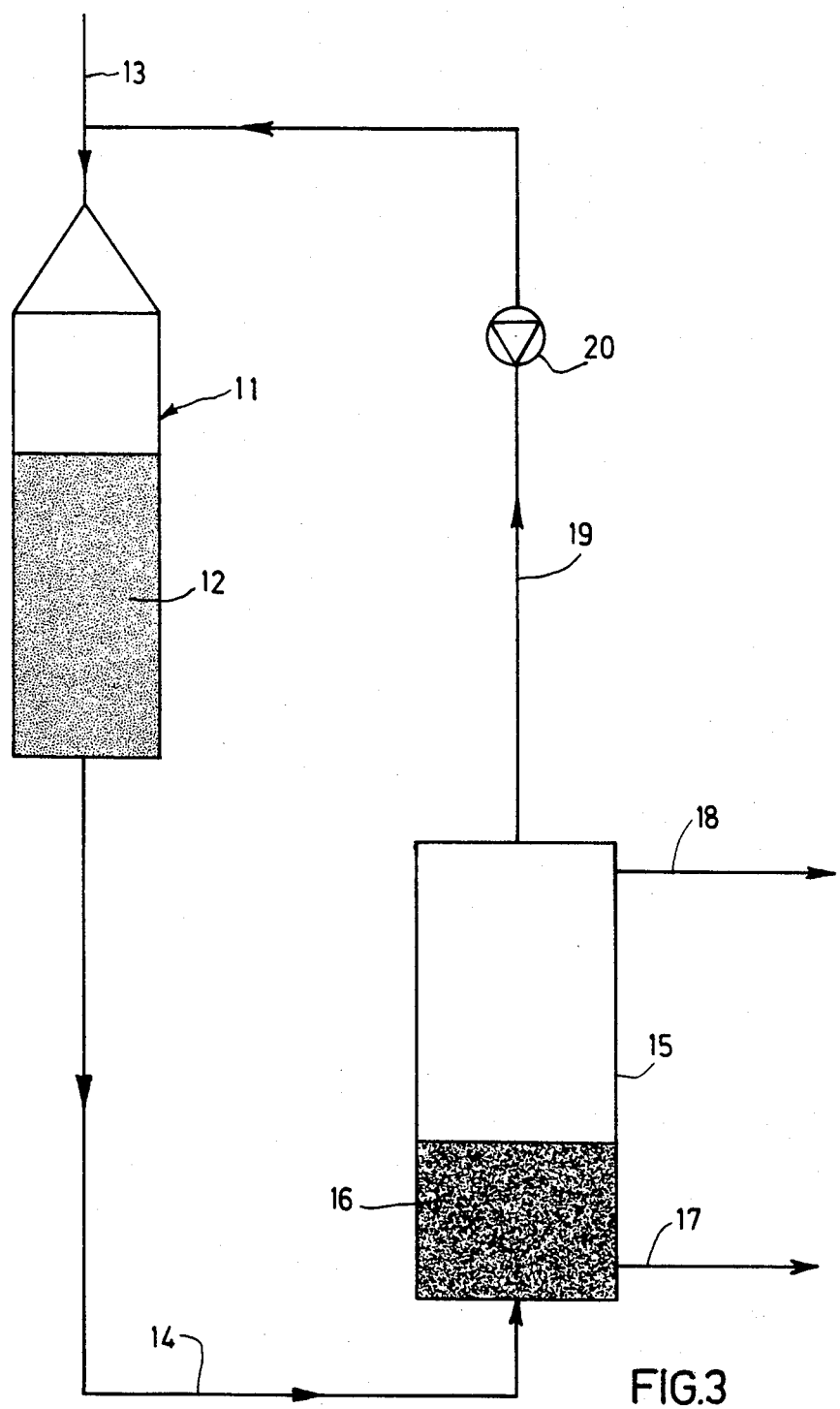
FIG. 3 shows another form of carrying out this method. Best mode of carrying out the invention Reference is first made to FIG. 1 in which a column 1 is shown wherein a granular layer 2 is provided, which is of a material whose nature, volume and granulometry are chosen as a function of the desired result and of the suspension to be treated. It can, for example, be constituted of natural sand (quartz or quartzite) of a granulometry between 0.2 and 4 mm.

The invention can, however, also be carried out with the granular layer being traversed from top to bottom suspension of microscopic particles to be flocculated. FIG. 3 shows this embodiment.

In this embodiment, the column 11 which contains a granular layer 12 is at its upper portion supplied by a conduit 13 with a liquid containing the microscopic particles in suspension. The outflow containing the flakes of flocculated particles is evacuated at the base of the column 11 by a conduit 14 in direction of the lower portion of a vertical separator 15 and is removed by a conduit 17. The partially purified liquid is evacuated at the upper portion of the separator by a conduit 18, and a portion of this liquid may by recycled, as before, by a conduit 19 and a pump 20 toward the supply conduit 13 of the column 11.

The following examples illustrate various applications of the method according to the invention:

EXAMPLE I

This example concerns the application of the above method to the collection of phyto-plankton microalgae in suspension in water.

Many tests have been carried out with different types of granular layers in a vertical column with ascending flux, with microalgae suspended in the water. The following table shows the results of these tests and makes the efficiency of the method according to the invention clear.

granular layer of calcinated and crushed clay of great granulometry (3 to 5 mm) is in a surprising manner especially advantageous for carrying out the method.

The invention thus provides a simple method, easy to carry out and of low cost, for concentrating suspensions with very small concentrations of microscopic particles. It is clear that the present method is particularly interesting in its application for the collecting of microalgae or of zooplankton, because it does not alter in any way the physical-chemical properties of the recovered microorganisms since they remain in a living state in their natural habitat during the entire length of the concentrating and collecting operations.

EXAMPLE II

This example concerns the application of the method according to the invention to the purification of used city water which has undergone a preliminary clearing up by simple decantation.

This type of water which has a concentration of suspended matter varying between 150 to 200 mg/l, passes through a fixed layer of sand with a granulometry of 300 $\mu$m, without addition of any flocculation reagent.

A rate of expansion of 10% of the sand layer is noted.

It is noted that 50% of the suspended materials are retained at a passing time of one hour, whereas 70% of these materials are retained at a passing time of 3 hours.

The suspended materials which are retained form a flocculate which is deposited at the surface of the granular layer. This flocculate can be periodically or continuously removed.

We claim:

1. Method of treating microscopic particles comprising micro-organisms in suspension in a liquid, comprising: passing a first liquid containing said microscopic particles in suspension through a fixed granular layer up to partial or complete clogging of said granular material by said microscopic particles; passing a second liquid through said fixed layer to be partially unclogged by the passing of said second liquid therethrough; said second liquid moving in the same direction as the first liquid, but at a higher speed so as to recover below said layer in the direction of passage of said liquid, flocculated aggregates of said microscopic particles and an outflow of a liquid which is freed of said particles.

2. Method according to claim 1, wherein said second liquid contains microscopic particles in suspension.

3. Method according to claim 2, wherein said first and said second liquid are one liquid.

4. Method according to claim 3, wherein a portion of the liquid is recycled for supplying said granular material.

TABLE

| Type of granular layer | Granulometry (mm) | Speed of flux at empty column (m/h) | Expansion (%) | Concentration at input of column (mg/l) | Concentration after flocculation and decantation in test tube (10 mm) (mg/l) | Rates of concentration |
| --- | --- | --- | --- | --- | --- | --- |
| Calcinated crushed clay | 3–5 | 1 | 0 | 200 | 50 000 | 250 |
| Ceramic | 1–2 | 1 | 0 | 100 | 20 000 | 200 |
| Sand | 0.2–0.25 | 0.25 | 10 | 60 | 8 400 | 140 |
|  |  | 0.50 | 15 | 100 | 1 400 | 140 |
|  |  | 1 | 20 | 100 | 1 400 | 140 |

This table shows the efficiency of the method according to the invention and indicates in particular that a 5. Method according to one of claims 1 to 4, wherein said granular material is passed through bottom to top by said first and said second liquid.

6. Method according to claim 5, wherein said granular material is fixedly arranged during the operation of the method.

7. Method according to claim 5, wherein said granular material undergoes an expansion of 30% in volume.

8. The method of claim 1, said liquids being free of flocculating agents.

9. Method of treating microscopic particles in suspension in a liquid, comprising: passing a first liquid containing microscopic particles in suspension through a fixed granular layer up to partial or complete clogging of said granular material by said microscopic particles; passing a second liquid through said fixed layer to be partially unclogged by the passing of said second liquid therethrough; said second liquid moving in the same direction as the first liquid, but at a higher speed so as to recover below said layer in the direction of passage of said liquid flocculated aggregates of said microscopic particles and an outflow of a liquid which is freed of said particles, wherein the speed of passing of the second liquid through the granular material is about 0.1 to 5 m/h.

10. Method according to claim 9, wherein said granular material is formed of particles having a granulometry of about between 0.005 and 3 cm and a volume of about 1.1 g/cm$^3$ or more.

11. Method according to claim 10, wherein said granular material is formed of calcinated and crushed clay of a granulometry between 3 and 5 mm.

12. Method according to claim 11, wherein said granular material is provided in a column (1), vertical or inclined, cylindrical or helical, whose portion situated above said material has a greater cross-section that the one containing said material.

13. Use of the method according claim 9 for collecting microalgae and zooplankton, whereby said flocculate is then concentrated by liquid-solid separation means.

14. Use of the method according claim 9 to purifying used water in the absence of any flocculation reagent.

* * * * *